Figure 1:
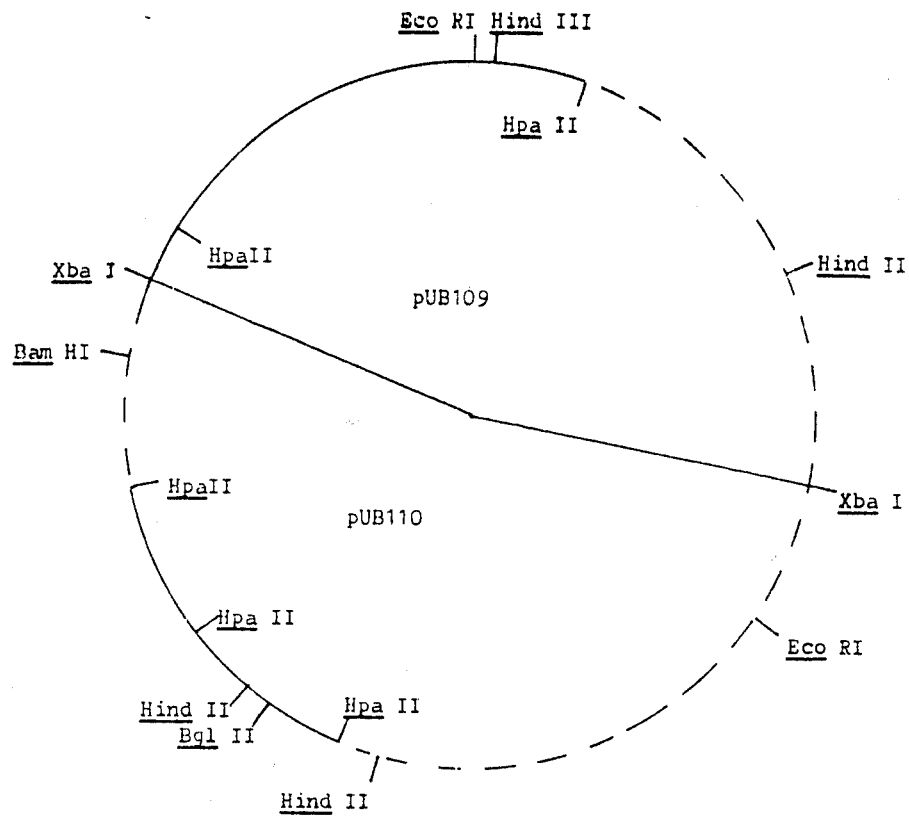

United States Patent [19]

Sanders et al.

[11] 4,430,434
[45] Feb. 7, 1984

[54] PLASMID AND ITS USE

[75] Inventors: Johan P. M. Sanders, Delft, Netherlands; Andrew J. P. Docherty, Bristol, England

[73] Assignee: Gist Brocades NV, Wateringseweg, Netherlands

[21] Appl. No.: 147,483

[22] Filed: May 7, 1980

[30] Foreign Application Priority Data

May 11, 1979 [GB] United Kingdom ............... 7916377

[51] Int. Cl.$^3$ .................. C12N 1/20; C12N 15/00; C12N 1/00; C12P 21/00

[52] U.S. Cl. ........................ 435/253; 435/68; 435/172; 435/317

[58] Field of Search .................. 435/172, 68, 317, 834

[56] References Cited

U.S. PATENT DOCUMENTS 4,237,224 12/1980 Cohen et al. .................... 435/849

OTHER PUBLICATIONS

Barth; in *Plasmids of Medical, Environmental, and Commercial Importance*, Timmis et al., (ed.), Elsevier/North-Holland, Amsterdam, 1979, pp. 399–410.
Gryczan et al., J. Bact. 134, 318 (1978).
Keggins et al., Proc. Natl. Acad. Sci. U.S.A. 75, 1423 (1978).
Suttcliffe et al., in *Genetic Engineering*, Chakrabarty (ed.), CRC Press, 1979, pp. 83–101.

*Primary Examiner*—David M. Naff
*Assistant Examiner*—James Martinell
*Attorney, Agent, or Firm*—Robert E. Burns; Emmanuel J. Lobato; Bruce L. Adams

[57] ABSTRACT

Plasmid conferring resistance to streptomycin ($Sm^R$) and neomycin ($Neo^R$) upon its host (e.g. a *Bacillus, Staphylococcus* or *Escherichia coli*) and which after having taken up a foreign DNA fragment at one of its restriction sites with loss of its $Sm^R$ or $Neo^R$ phenotype, is still capable of replicating and expressing genetic information in its host.

21 Claims, 2 Drawing Figures

PLASMID AND ITS USE

DESCRIPTION

This invention relates to a new plasmid and to its use as a cloning vehicle.

Plasmids are circular molecules of DNA found in cells of certain microorganisms. In recent years their importance has grown, due to their role as a tool for genetic engineering. It has appeared that with suitable techniques some plasmids can be enriched with new genetic information and transformed to a special host microorganism, where the new genes can be replicated and expressed. This procedure is referred to as cloning. The hosts which have received special attention are those microorganisms which play an important role in fermentation technology such as bacteria belonging to the genus Bacillus. The plasmids used for cloning preferentially contain selective markers. Selective markers are genes which cause distinguishing marks in the phenotype of the microorganism, such as resistance to certain antibiotics. When the cloning procedure has succeeded a marker gene is inactivated. Therefore microorganisms with inserted genes can easily be selected because they have a different phenotype such as sensitivity for the antibiotic related to the originally selective marker.

Few naturally occurring plasmids carrying selective markers have been described in the literature for the genus Bacillus (cf. Bernhard et al, J. Bact. 133 (1978) p. 897–903, and Hegarath and Anagnostopoulis, Molec. gen. Genet. 157 (1977) p. 167–174).

Plasmids from other species such as *Staphylococcus aureus* have been successfully transformed into *Bacillus subtilis*. Some of them remain stably in their new host and express a selective marker (cf. Ehrlich, Proc. Natl. Acad. Sci. U.S.A. 74 (1977) p. 1680–1682, and Gryczan et al, J. Bact. 134 (1978) p. 318–329). Those plasmids introduced into *B. subtilis* which do reside stably and exist as an autonomous multicopy replicon can only be used for the simplest of cloning operations. This is because many of these plasmids carry only one marker (Keggins et al, Proc. Natl. Acad. Sci. U.S.A. 75 (1978) p. 1423–1427). This makes screening or selection for recombinants by change in host cell phenotype due to gene inactivation or other alteration impossible.

On the other hand for those plasmids introduced into *B. subtilis* which contain more than one marker, no gene inactivation has been described.

Therefore it is an object of this invention to provide a plasmid, derived from plasmids already described, in which gene inactivation, leaving a second selectable marker, is possible in its host, e.g. Bacillus. Such a plasmid will allow the insertion, replication, expression and amplification of DNA fragments from a wide variety of sources in the host of choice. Consequently, by having this ability to manipulate DNA sequences, it is possible to control the synthetic output of the selected host cell.

According to the present invention, a new plasmid is provided conferring resistance to streptomycin ($Sm^R$) and neomycin ($Neo^R$) upon its host or, after having taken up a foreign DNA fragment at one of its restriction sites with loss of its $Sm^R$ or $Neo^R$ phenotype, still capable of replicating and expressing genetic information in its host, the host being, e.g. Bacillus, such as *B. subtilis*, *B. licheniformis* or *B. amyloliquefaciens*, or Staphylococcus or *Escherichia coli*. This plasmid fulfills the aforementioned requirements, and it may be built up from a plasmid conferring $Sm^R$ and a plasmid conferring $Neo^R$, each being derived from *Staphylococcus aureus* or *Bacillus cereus*. The streptomycin gene (Sm) has at least one site for a restriction endonuclease useful for inserting new fragments of DNA. A restriction endonuclease which cuts at this particular site is Eco RI. Another one is Hind III. Insertion of DNA into these sites inactivates the Sm gene. The neomycin gene ($Neo^R$) has such a useful site which is recognized by Bgl II. The Neo gene is inactivated when DNA is inserted into this site. Other restriction sites may be useful to insert foreign DNA fragment, inactivating the $Sm^R$ or $Neo^R$ phenotype.

The plasmid according to the invention is useful for replication of the new DNA fragment in its host, e.g. Bacillus such as *B. subtilis*, *B. licheniformis* or *B. amyloliquefaciens*, or Staphylococcus or *Escherichia coli*. Cells containing this plasmid in which new DNA has been inserted can be detected by the phenotype streptomycin sensitive ($Sm^S$) and $Neo^R$ or $Sm^R$ and neomycin sensitive ($Neo^S$). A specific example of a plasmid according to the invention is one having the designation pUB1654. This plasmid is deposited in a Bacillus host with the Centraal Bureau voor Schimmelcultures, Oosterstraat 1, 3742 SK Baarn, the Netherlands, under the number CBS 237.79. The invention also relates to mutants and variants thereof having the properties indicated hereinbefore, as well as to those plasmids having inserted therein a foreign DNA fragment. The invention further relates to plasmids as indicated being introduced into a host, e.g. one of the above-indicated miroorganisms, and replicating and expressing therein.

According to another feature of the present invention, a process for preparing a plasmid as hereinbefore indicated, comprises the preparation of, on the one hand, a plasmid conferring $Sm^R$ and, on the other hand, a plasmid conferring $Neo^R$, introducing each of such plasmids into a host, where they are amplified, isolating the plasmids therefrom, restricting the plasmids with a restriction enzyme not interfering with the gene properties as to $Sm^R$ and $Neo^R$ of the starting plasmids, recombining the restricted plasmids and selecting or screening the recombined plasmid conferring $Sm^R$ as well as $Neo^R$. The plasmid obtained may be used for taking up a foreign DNA fragment into one of its restriction sites, still replicating and expressing in its host. The host used in the preparation process may be one of the microorganisms indicated above, and is preferably the restrictionless *B. subtilis* 1G20, which does not contain restriction enzymes which can degrade incoming foreign DNA. The starting plasmids may be derived from several microorganisms, e.g. *Staphylococcus aureus* or *Bacillus cereus*.

Plasmids from a wide variety of sources were transformed into *B. subtilis* strain 1G 20 (cf. Bron and Venema, Mutation Res. 15, (1972) p. 1–10) using the classical methods of Anagnostopoulos and Spizizen (cf. J. Bact. 81 (1961) p. 741–746). Their ability to replicate autonomously and express their selective markers (generally antibiotic or heavy metal ion resistance) previously detected in their primary host was observed. Two such plasmids were from *Staphylococcus aureus*. One, called pUB109, confers $Sm^R$ on its staphylococcal host while the other, pUB110, confers $Neo^R$. Both plasmids were found to replicate autonomously in, for example, *B. subtilis* where they exist in high copy number.

pUB109 conferred the phenotype $Sm^R$ and pUB110 the phenotype $Neo^R$ on their *B. subtilis* hosts into which they were inserted. The expression and replication of pUB110 in *B. subtilis* has been reported by Gryczan et al (J. Bact. 134 (1978) p. 318–329). After re-isolating pUB109 and pUB110 plasmid DNA from *B. subtilis* 1G 20 the recombinant pUB1654 was made by restricting them into linear molecules and ligating them into a recombinant plasmid in vitro. It has been observed that restriction of the plasmids pUB109 and pUB110 with the restriction endonuclease Eco RI does not lead after ligation to a composite plasmid with the desired properties, whereas restriction with Xba I does lead to formation of new plasmid pUB1654. It has also been observed that some DNA is lost by ligating the restricted plasmids pUB109 and pUB110 to pUB1654, since the molecular weight has been estimated to be $3.75 \times 10^6$, whereas the sum of the molecular weights of pUB109 and pUB110 is $5.8 \times 10^6$. Apparently the DNA structures conferring $Sm^R$ and $Neo^R$ have been retained in pUB1654, although one restriction site for each Eco RI and Xba I has been lost.

As indicated hereinbefore the new plasmids according to the invention (e.g. pUB1654) are capable of being used for insertion of foreign DNA fragments in the Eco RI on Hind III sites of the $Sm^R$ gene of the molecule, or the Bgl II site of the $Neo^R$ gene. By such insertion it is possible to use the thus obtained plasmids in a host, e.g. a Bacillus host, to express certain properties which are desirable in industry e.g. higher yields in microbiological production of certain enzymes.

The new plasmid pUB1654 appears to be temperature sensitive in replication. This property stems from the $Sm^R$ gene of the original plasmid pUB 109. It is therefore recommended not to store pUB 1654 carrying microorganisms at temperatures over 30° C. Due to this property microorganisms can be tested on the presence of pUB 1654 with inserted cloned genes by growing them at a temperature of 45° C. The test is positive if the newly acquired trait appears to have been lost.

Figure 2:
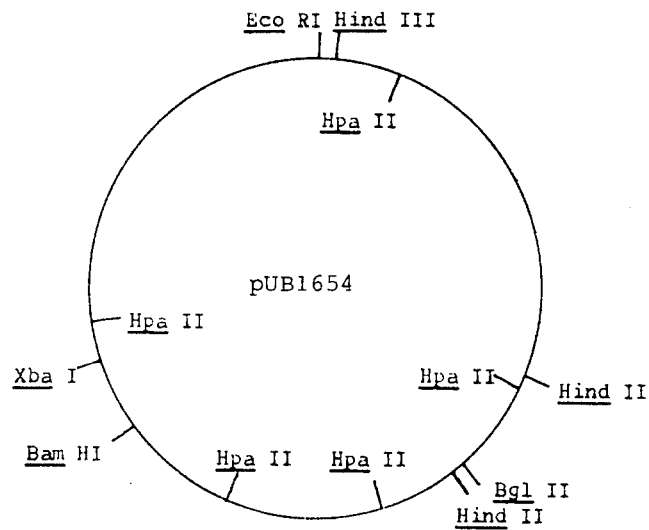

The invention is illustrated by the following Example, reference being made to the attached drawings in which FIG. I shows the restriction map of the composite plasmids pUB 109 and pUB 110 (the interrupted parts of the circle showing those parts of the original DNA molecules which are deleted in the composite plasmid) and FIG. 2 shows a restriction map of pUB1654.

EXAMPLE

1. Preparation of Plasmid DNA Isolated from *B. subtilis* 1 G 20

500 ml of double strength L-broth (20 g/l of Tryptone, 10 g/l of yeast extract and 20 g/l of NaCl) containing 5 µg/ml Neo was inoculated with *B. subtilis* 1G 20 harboring the previously transformed pUB 110. Similarly 500 ml of double strength L-broth containing 50 µg/ml Sm was inoculated with *B. subtilis* 1G 20 harboring pUB 109. The cultures were grown overnight with shaking at 37° C.

In the morning the cells were harvested by centrifugation and resuspended in 7.5 ml of 25% sucrose, 0.05 M of Tris-HCl, pH 8.0. 1.5 ml of lysozyme 50 mg/ml in 0.25 M of Tris-HCl, pH 8.0, and 3.0 ml of 0.25 M ethylenediaminetetra-acetic acid (EDTA) pH 8.0. The lysozyme treatment was continued for 15 minutes at 4° C.

0.1 ml of 2.5 mg/ml ribonuclease-A (RNase from bovine pancreas) in water was added. The RNase had previously been heated at 60° C. for 30 minutes to destroy any contaminating deoxyribonuclease (DNase) activity.

12.0 ml of 0.5% Triton X-100 in 0.05 M of EDTA and 0.05 M of Tris-HCl, pH 8.0, were added. After mixing, the suspension was kept at 4° C. for 20 minutes. Then 2.5 ml of 5 M sodium chloride (NaCl) were added. The addition of the NaCl brought about cell lysis.

The cell debris, including cell walls, membrane and attached chromosome, etc. was separated from the supernatant by centrifugation at 45,000 g for 60 minutes at 4° C. The cleared lysates (supernatants) were collected from the centrifuge tubes. Polyethylene glycol (PEG) 6000 was added to the cleared lysates to a final concentration of 10% weight for volume.

When the PEG 6000 had dissolved the DNA preparations were kept at 4° C. for 3 hours. During this time a complex precipitate of PEG and plasmid DNA formed. It was removed from the liquid phase by centrifugation at 20,000 g for 15 minutes at 4° C. The supernatant was discarded.

The pellet was resuspended in 7 ml of 10 mM Tris-HCl, 0.5 mM of EDTA and 7 ml of chloroform were added and shaken gently for 5 minutes. The aqueous upper phase was removed after centrifugation at 40,000 g for 15 minutes. The PEG 6000 present pelleted at the interface and was discarded with the lower chloroform phase. This chloroform extraction was repeated.

5.8 ml of the upper phase were added to 6 g of cesium chloride which dissolved. 0.2 ml of 10 mg/ml ethidium bromide in water was added. This resulted in a volume of approximately 7.5 ml which was centrifuged for 36 hours at 4° C. at 110,000 g.

After 36 hours two distinct fluorescent bands were observed in the tubes of cesium chloride solution (which had formed a density gradient) when they were held in front of an ultra violet light source. This is because chromosomal DNA binds within its molecular structure more ethidium bromide than super-coiled plasmid DNA. As a consequence the chromosomal DNA is relatively less dense and bands higher in the cesium chloride density gradient. The position of the two DNA types (which have been isolated originally from the lysed cells) is visible since it is their bound ethidium bromide that fluoresces.

In each case the lower plasmid band was removed with a syringe and hypodermic needle. The plasmid DNA was now in a volume of approximately 0.5 ml of cesium chloride solution.

The bound ethidium bromide was removed by extracting 3 times with an equal volume of isopropanol saturated with cesium chloride. The volume was then increased to 2 ml by the addition of 10 mM of Tris-HCl, 0.1 mM of EDTA and 0.2 ml of 4 M sodium acetate, pH 6.0, in water. This was followed by 6 ml of cold (−20° C.) ethanol. In these conditions any DNA present (which should be purified plasmid DNA) precipitates. The tubes were kept at −20° C. overnight.

In the morning the precipitates were spun down at 10,000 g at −20° C. for 20 minutes. The supernatants were poured off and the tubes left inverted to dry. Having dried, the precipitates (generally invisible) were resuspended in 0.5 ml of sterile 10 mM Tris-HCl, 0.1 mM of EDTA. 2 µl samples were mixed with 5 µl of a solution containing 0.2 M of EDTA, 35% Ficoll and 0.5 mg/ml of bromophenol blue (stopping buffer). The DNA samples were then placed on a 0.9% agarose gel and electrophoresis proceeded. Visualization with UV light indicated each preparation was plasmid DNA of characteristic molecular weight and consequent mobility on the gel.

2. Restriction Analysis of pUB109 and pUB110

Plasmid DNA prepared as described was digested with a variety of restriction endonucleases and analyzed on agarose gels. As a result restriction maps of pUB109 and pUB110 were drawn up as shown in FIG. 1.

The restriction endonucleases Hpa II and Hae III were obtained from Miles. Hind III, Hind II, Cau II, Xba I and Bgl II were obtained from Dr. A. Atkinson (MRE, Porton). Bam HI, Taq I and Eco RI were prepared from the appropriate strains by standard procedures and stored at $-20°$ C. in 50% glycerol, 0.5 M of NaCl, 0.01 M of potassium phosphate. All restriction digests were carried out in a buffer system of final concentration 50 mM of Tris-HCl, 5 mM of $MgCl_2$, pH 7.5, at $37°$ C. (cf. Grindsted et al, Molec. gen. Genet. 166 (1978) p. 313–320). On completion digestions were mixed with 5 $\mu$l stopping buffer and loaded onto an agarose gel. Concentrations of agarose were between 0.7 and 1.5% (w/v) depending on the size of the fragments to be analyzed. A molecular weight marker of bacteriophage $\lambda$ DNA digested with Bgl I was used. The marker sizes were a personal communication from C. L. Choi, Department of Bacteriology, Bristol.

3. Prepartion of pUB109 and pUB110 DNA molecules linearized at their Eco RI sites 10 $\mu$g pUB110 DNA was linearized with approximately 10 units of the restriction endonuclease Eco RI in a buffer system of final concentration 100 mM of Tris-HCl, 50 mM of NaCl, 10 mM of $MgCl_2$. Restriction was carried out at $37°$ C. for 60 minutes. Similarly 10 $\mu$g pUB109 was linearized with Eco RI.

4. Preparation of pUB109 and pUB110 DNA molecules linearized at their Xba I sites 10 $\mu$g pUB110 plasmid DNA was linearized with approximately 10 units of the restriction endonuclease Xba I in a buffer system of final concentration 50 mM of Tris-HCl, 5 mM of $MgCl_2$. Restriction was carried out at $37°$ C. for 60 minutes. Similarly 10 $\mu$g pUB109 was linearized with Xba I.

5. Assay for Completion of Linearization by Either Eco RI or Xba I

After 60 minutes all the reactions described above were stopped by placing the tubes containing the DNA and restriction enzyme on ice. A sample was taken containing 1 $\mu$g DNA from each tube and added to 5 $\mu$l stopping buffer. Each sample was then loaded onto a 0.9% agarose gel to check for complete linearization. This resulted in conversion of the super-coiled circular DNA molecules to a linear molecule running slower on the gel. This single band was estimated to represent a linearized molecule of a molecular weight of $3.0 \times 10^6$ for pUB110 and $2.8 \times 10^6$ for pUB109 by comparing the fragments of a $\lambda$ DNA digestion with Hind III which was also run on the same gel and whose linear fragments are of known molecular weight.

Where necessary digestion of pUB109 or pUB110 was continued by removing the samples from the ice and incubating at $37°$ C. until digestion was complete as estimated by the gel assay. When the pUB109 and pUB110 DNA had all been shown to have been linearized by either Xba I or Eco RI the enzymes were inactivated by heating the DNA preparations at $60°$ C. for 10 minutes.

6. Joining of the molecules (ligation) and consequent Formation of the recombinant molecule pUB1654

5 $\mu$g of pUB110 linearized at its Eco RI site was mixed with 5 $\mu$g of pUB109 linearized at its Eco RI site, both prepared as described above. The DNA was precipitated from this mixture by adding 11% (v/v) 3 M of sodium acetate pH 6.0 and isopropanol 60% (v/v). Precipitation was carried out at $-20°$ C. for 20 minutes.

5 $\mu$g of pUB110 linearized at its Xba I site was mixed with 5 $\mu$g of pUB109 linearized at its Xba I site and the DNA precipitated as described above.

The precipitates were separated from the supernatants by centrifugation. The precipitates were then left to dry for 20 minutes in an evacuated desiccator. The precipitates were resuspended in 7 $\mu$l of sterile water to which was added 1 $\mu$l of 10$\times$ ligase buffer followed by 2 $\mu$l of T4 ligase (made from T4 infected *Escherichia coli* B and obtained from Miles) (approximately 1000 units/ml). The 10$\times$ ligase buffer contained 660 $\mu$l 1 M of Tris-HCl, 50 $\mu$l 0.2 M of EDTA, 100 $\mu$l 1.0 M of $MgCl_2$, 20 $\mu$l of 50 mg/ml Bovine Albumin Powder (BSA, viz bovine serum albumin), 10 $\mu$l of 0.1 M adenosine 5'-triphosphate (ATP), 100 $\mu$l of 10 M DL-dithiothreitol (DTT) and 60 $\mu$l of sterile water. All the reagents were sterile as a result of autoclaving, or filtration in the case of BSA, ATP and DTT. The sterile Tris-HCl was such that it would give a pH value of 7.2 to 7.8 in the temperature range of $0°$ to $20°$ C.

The ligating DNA mixtures were placed in a water bath at $20°$ C. which was placed in a cold room at $4°$ C. Overnight the temperature in the water bath slowly fell until it reached $4°$ C. after approximately 18 hours. After being left to ligate overnight, the DNA was re-precipitated in the morning. The volumes were increased to 50 $\mu$l by the addition of 40 $\mu$l of sterile 10 mM Tris-HCl, 0.5 mM of EDTA. Precipitation was as before using 3 M sodium acetate 11% (v/v) and isopropanol 60% (v/v). The precipitates were dried down as before.

The precipitates were then resuspended in 10 $\mu$l 10 mM of Tris-HCl, 0.5 mM of EDTA. 50 $\mu$l of 50% PEG 1500 was added and the DNA/PEG mixture held at $60°$ C. for 10 minutes to kill any contaminating nucleases or bacterium in the mixture or in the small tube in which it was contained. The mixture was then left overnight at $-20°$ C.

7. Transformation of *Bacillus subtilis* strain 1G 20

1G 20 is a strain of *Bacillus subtilis* which can grow in a Minimal Salts medium provided there is a carbon source such as glucose, and the amino acid tryptophan is present (cf. Bron and Venema, Mutation Res. 15 (1972) p. 1 to 10). 1G 20 also has a special characteristic—it is restrictionless. This means that it does not degrade incoming DNA with restriction endonucleases during the DNA uptake that occurs during transformation.

In order to transform 1G 20 it is necessary first to render the strain competent. A competent strain is one in which its physiological state is such that it will take up DNA from its immediate environment. Two kinds of media are necessary to achieve this state of competence in 1G 20.

(A) Growth Medium (GM): 95 ml of Minimal Salts (2×), 1.0 ml of 20 mg/ml tryptophan, 2.0 ml of 20% glucose, 2.0 ml of 0.8% casein hydrolysate and 40 µl of 0.3 g/ml yeast extract. (Double Strength Minimal Salts Medium consists of 14.0 g of $K_2HPO_4$, 6.0 g of $KH_2PO_4$, 0.5 g of $MgSO_4$, 2.0 g of $(NH_4)_2SO_4$, 1.0 g of trisodium citrate and 8.0 g of glucose per 1 liter of deionized water, pH 7.0. The glucose is autoclaved separately and added as a 40% solution in distilled water).

(B) Transformation Medium (TM): 50 ml of Minimal Salts (2×) and 5.0 ml of 5.5% glucose. A single colony of 1G 20 was inoculated into 20 ml of GM and grown up overnight in a shaking flask at 37° C. In the morning the culture was diluted with 15 ml of fresh GM. The culture now had an optical density of 0.8 at 450 nm ($A_{450}$). The flask was now well aerated by vigorous shaking in an incubator at 37° C. One hour later 0.5 ml of 0.8% sterile casein hydrolysate was added. The $A_{450}$ was found to be increasing at a rate of 0.3 per hour.

After 2 hours the rate of $A_{450}$ change began to slow down. After 2 to 3 hours it had fallen to a rate of 0.2 per hour and an $A_{450}$ of 1.6 was reached. At this point 20 ml of the 1G 20 culture were added to 20 ml prewarmed TM in a fresh flask. Vigorous aeration at 37° C. was continued for another 90 minutes. 0.2 ml samples of the 1G20 culture were then added to the DNA/PEG mixtures in their small sterile tubes. 0.2 ml of culture was also added to a sterile tube containing only 50 µl of 50% PEG 1500 and 10 µl of sterile water.

The tubes were shaken vigorously for one hour. 1.8 ml of prewarmed double strength L-broth (20 g/l of tryptone, 10 g/l of yeast extract and 20 g/l of NaCl) was then added to the tubes. Incubation was continued at 37° C. The L-broth is very nutritious for the 1G 20 cells and allows them to start growing and dividing more rapidly. The cells were physiologically in a state of starvation due to the regime used to induce competence and during transformation, prior to this addition. During this period of growth any new plasmid DNA that may have been taken up by the cells may have the opportunity to stabilise, replicate and express its genes. Some of these genes may confer a resistance to an antibiotic on their host cell. Consequently any 1G 20 cells that have taken up plasmid DNA from the PEG mixture should now become resistant to that antibiotic. This period of growth after DNA uptake is called the period of gene expression.

After 1.5 hours of gene expression 1 ml was removed from each tube and added to 9 ml of double strength L-broth, a dilution of 1 in 10. 0.1 ml was then spread on agar plates (Heart infusion Agar, Difco, Detroit, U.S.A.) containing antibiotics as shown in Table 1. The plates were incubated overnight at 37° C. Results (averaged from 5 plates) are shown in Table 2.

In the same way B. subtilis 1G20 was transformed with plasmid pUB110. After the period of gene expression, the liquid was diluted with double strength L-broth and plated as described above.

TABLE 1

| 1G 20 transformed with | Agar plates containing the following antibiotics 0.1 ml of a 1/10 dilution plated | | |
|---|---|---|---|
| | neomycin (5 µg/ml) | streptomycin (50 µg/ml) | neomycin (5 µg/ml) streptomycin (50 µg/ml) |
| pUB110 | 5 plates | 5 plates | 5 plates |
| pUB110 and pUB109 ligated at their Xba I sites | 5 plates | 5 plates | 5 plates |
| pUB110 and pUB109 ligated at their Eco RI sites | 5 plates | 5 plates | 5 plates |
| No DNA | 2 plates | 2 plates | 2 plates |

TABLE 2

| 1G 20 transformation | Nutrient agar Neo5 | Nutrient agar Sm50 | Nutrient agar Neo5, Sm50 |
|---|---|---|---|
| pUB110 | 1 colony per plate i.e. 1 × $10^2$ $Neo^R$ transformants per ml plated | Several small colonies Background growth | Several small colonies Background growth |
| pUB110 × Xba 1 × pUB109 | 14 colonies per plate, i.e. 1.4 × $10^3$ $Neo^R$ transformants/ml plated | Background growth as with control | 6 colonies per plate i.e. 6 × $10^2$ $Neo^R$ $Sm^R$ transformants/ml plated |
| pUB110 × Eco RI × pUB109 | 15 colonies per plate, i.e. 1.5 × $10^3$ $Neo^R$ transformants/ml plated | Background growth as with control | Several small colonies Background growth |
| No DNA | No growth | Background growth | No growth |

1G 20 transformed with pUB110 resulted in $Neo^R$ colonies. Therefore during the transformation the 1G 20 culture was competent for uptake of plasmid DNA.

When transformed withh pUB110 ligated with pUB109 at their Xba I sites colonies resulted that were $Neo^R Sm^R$. They may be spontaneous mutants to resistance. They may have received two plasmid molecules—one pUB110 and one pUB109, independently. Each confers its respective resistance $Neo^R$ and $Sm^R$. Or a recombinant plasmid resulting from the ligation may have been transformed. This single plasmid carries genes such that it confers resistance to Neo as well as Sm.

When transformed with pUB110 ligated with pUB109 at their Eco RI sites no $Neo^R Sm^R$ colonies were obtained. Only $Neo^R$ colonies were conclusively demonstrated. If the ligation was efficient this indicates that insertion of DNA (in this case the puB110 molecule) at the Eco RI site of pUB109 inactivates the $Sm^R$ gene.

When competent 1G 20 cells were mixed with PEG 1500 but no DNA, no colonies resistant to Neo were obtained. Although there was background growth on the Sm plates this was due to background resistance in the strain. There was no growth on the Sm,Neo plates. The Sm plates appeared to have a lot of background growth which made comparison impossible.

8. Evaluation of pUB1654

500 ml cultures containing neomycin 5 µg/ml and and streptomycin 50 µg/ml in double strength L-broth were grown up from several of the Neo$^R$Sm$^R$ 1G 20 clones resulting from the Xba I ligation. Plasmid DNA was prepared as previously described and 2 µl samples analyzed on 0.9% agarose gels. On the same gels a sample of pUB110 plasmid DNA was placed. Three of the new plasmid preparations examined produced super-coiled DNA plasmid bands running slower in the gel than the super-coiled plasmid DNA of pUB110. This indicated that indeed a new molecule had been created, as a result of the ligation, that was larger than either of the parent molecules (pUB109 is smaller than pUB110).

As can be seen from the restriction map of the two parent molecules in FIG. 1 a hybrid of the two should contain a single Hind III site. Therefore the new plasmid DNA preparations were digested with Hind III which should linearize the circular molecule to give us an estimate of its molecular weight. The linearized DNA preparations were run on a 0.9% agarose gel together with a Hind III digestion of λ bacteriophage DNA which gives fragments of known size. As expected the new DNA preparations gave a single band representing the linearized molecule. However, by comparison with the λ digested with Hind III bands, the new molecule had a molecular weight of approximately $3.75 \times 10^6$ in each of the three new plasmid preparations. $3.75 \times 10^6$ is larger than either of the parent molecules but less than their sum, which would have been $5.8 \times 10^6$. Therefore there had certainly been created new plasmid molecules which from the phenotype carried antibiotic resistance genes from both parents, but which were not simply the sum of both parent molecules.

Evaluation to establish which regions of each parent plasmid were joined together and which pieces were missing was continued. It is clear that an Xba I digestion of the new molecule should result in the production of two fragments—one from each parent—since the original ligation was through the parent Xba I site. Similarly, if the new plasmids were the sum of the parent molecules an Eco RI digestion would give two fragments, since an examination of the restriction maps reveals that each carries a single Eco RI site. Their sum should therefore carry two sites.

However, Eco RI and Xba I digestions of all of the three aforementioned new plasmids reveal that they only carry a single site for Eco RI and Xba U. Therefore if, during the ligation, the pUB110 and pUB109 molecules were joined through their unique Xba I sites it is clear now that after transformation a molecule is created that has a deletion of some of the parent DNA. Specifically there is loss of some DNA from the hybrid plasmid which carries one of the Xba I sites and one of the Eco RI sites.

A full analysis using the restriction enzymes Eco RI, Xba I, Bam HI, Hind III, Hind II, Cau II, Bgl II, Hpa II, Taq I and Hae III has been performed; a restriction map showing some of the restriction sites is shown in FIG. 2.

On transformation into *Bacillus subtilis* pUB1654 confers resistance to neomycin and streptomycin. Selection for 1G 20 transformants that have taken up pUB1654 can be made with 5 µg/ml neomycin and 100 µg/ml streptomycin. The plasmid has single sites for Bam HI, Xba I, Bgl II, Cau II, Hind III and Eco RI. It may have single sites for other restriction enzymes.

Earlier, as a result of obtaining no Neo$^R$Sm$^R$ transformants from the ligation of pUB110 and pUB109 through their Eco RI sites, it was postulated that a Eco RI site is within the streptomycin gene and that insertion of pUB110 DNA here inactivates the streptomycin resistance conferred by that sequence of DNA.

The restriction map of pUB1654 shows that the remaining Eco RI site in pUB1654 comes from the streptomycin resistance plasmid pUB109. This would be expected since the plasmid is phenotypically Sm$^R$ and it is proposed that this Eco RI site is part of the streptomycin gene's DNA sequence.

9. Testing of pUB1654 for insertional inactivation of streptomycin resistance at its Eco RI site Eco RI digests of λ DNA were ligated into pUB1654 at its Eco RI site. The conditions and methodology were as with the original ligation. The ligated DNA was transformed into 1G 20 and all the cells which had taken up DNA were selected on neomycin plates. The colonies which grew were tested for their sensitivity to streptomycin by plating them onto a nutrient agar plate containing 5 µg/ml neomycin and 100 µg/ml streptomycin.

Plasmid DNA was made from several of the Neo$^R$Sm$^S$ colonies. In all cases the plasmid content of these cells was a molecule larger than pUB1654. This indicated that new DNA had been added to the molecule. On digestion with Eco RI it could be demonstrated that new DNA had been inserted into the Eco RI site of pUB1654. By the Southern transfer technique (Southern, J. mol. Biol. 98 (1975) p. 503–517) it has been shown that this inserted DNA was phage λ DNA.

This indicates that pUB1654 can replicate DNA fragments in 1G 20 when randomly inserted into its unique Eco RI site. Also, the transformants that have taken up pUB1654 molecules which have had DNA randomly inserted into their Eco RI site can be recognized phenotypically from the outside of the cell due to those cells being streptomycin sensitive, neomycin resistant.

A further test of the vehicle pUB1654 has been carried out where Eco RI fragments of a tetracyclin resistant plasmid digestion were ligated with Eco RI-treated pUB1654. On transformation of 1G20 all the colonies which were selected for Neo$^R$ and Tet$^R$ were also Sm$^S$. Several of the colonies which were Neo$^R$ and Sm$^S$ were also Tet$^R$. Restriction analysis of the resulting colonies indicates that all the Neo$^R$ Tet$^R$ Sm$^S$ colonies contained pUB1654 with a DNA fragment from the tetracyclin plasmid carrying the tetracyclin resistance gene inserted into its Eco RI site, consequently inactivating the Sm$^R$ gene.

The colonies which were Sm$^S$ Neo$^R$ but not Tet$^R$ had inserted Eco RI fragments from the tetracyclin plasmid into the Eco RI site of pUB1654, but these particular fragments did not carry the tetracyclin gene.

pUB1654 has since been used for the replication of Eco RI digested chromosomal DNA from other Bacillus species within several *B. subtilis* strains. It is a very useful cloning vehicle because after having transformed pUB1654 molecules cut with Eco RI or with Hind III and ligated with Eco RI or HIND III respectively cut chromosomal DNA one can tell which colonies contain replicating multicopies of pUB1654 with inserted chromosomal DNA by nature of their Neo$^R$ Sm$^S$ phenotype.

An alternative way is to have the new plasmid restricted with Bgl II and ligated with Bgl II cut chromosomal DNA. After transformation it is the Neo$^S$Sm$^R$ phenotype which tells which colonies have replicating multicopies of pUB1654 which inserted chromosomal DNA.

We claim:

1. Plasmid conferring resistance to streptomycin (Sm$^R$) and neomycin (Neo$^R$) upon its host, constructed from derivatives or segments of plasmids pUB109 and pUB110, which is capable of replicating and expressing genetic information in Bacillus and which after having taken up a foreign DNA fragment at one of its restriction sites with loss of its Sm$^R$ or Neo$^R$ phenotype but not both, is still capable of replicating and expressing genetic information in its host.

2. Plasmid according to claim 1 wherein the Bacillus is *B. subtilis, B. licheniformis* or *B. amyloliquefaciens.*

3. Plasmid having the designation pUB1654, deposited with the Centraal Bureau voor Schimmelcultures at Baarn, Holland, under CBS No. 237.79, and mutants and variants thereof having the properties indicated, or having taken up therein a foreign DNA fragment at one of its restriction sites.

4. Plasmid according to any one of claims 1, 2, 3 or in which the foreign DNA fragment is inserted at its Eco RI restriction site.

5. Plasmid according to any one of claims 1, 2, 3 or in which the foreign DNA fragment is inserted at its Bgl II restriction site.

6. Bacillus host into which the plasmid according to any one of claims 1, 2, 3 or has been introduced.

7. The host according to claim 6, which is *B.subtilis, B.licheniformis* or *B.amyloliquefaciens.*

8. Plasmid according to one of claims 1, 2, 3 or in which the foreign DNA fragment is inserted at its Hind III restriction site.

9. The plasmid according to claim 1 which comprises an Eco RI restriction site within the Sm$^R$ gene.

10. The plasmid according to claim 1 which comprises a Hind III restriction site within the Sm$^R$ gene.

11. The plasmid according to claim 1 which comprises Eco R$_1$ and Hind III restriction sites within the Sm$^R$ gene.

12. The plasmid according to claim 1 which comprises a Bgl II restriction site within the Neo$^R$ gene.

13. The plasmid according to claim 1 which comprises Eco RI and Hind III restriction sites within the Sm$^R$ gene and a Bgl II restriction site within the Neo$^R$ gene.

14. The plasmid according to claim 10, 11 or 12 in which a foreign DNA fragment has been inserted at the restriction site.

15. The plasmid according to claim 1 wherein the host is *Bacillus subtilis.*

16. The plasmid according to claim 1 wherein the host is restrictionless *Bacillus subtilis* 1C 20.

17. Plasmid having the designation pUB 1654 as deposited with the Centraal Bureau vour Schimmelcultures at Baarn, Holland, under CBS No. 237.79 and mutants and variants thereof.

18. Plasmid having the designation pUB 1654, as deposited with the Centraal Bureau voor Schimmelcultures at Baarn, Holland under CBS No. 237.79 which has taken up a foreign DNA fragment at one of its restriction sites.

19. Bacillus harboring the plasmid according to claim 1, 3, 17 or 18.

20. The plasmid according to claim 13 in which a foreign DNA fragment has been inserted at one of said restriction sites.

21. The plasmid according to claim 1 which is constructed from derivatives or segments of plasmids pUB109 and pUB110 by restriction of said plasmids with the restriction enzyme Xba I and recombination of the thus restricted plasmids.

* * * * *